(12) United States Patent
Zhu et al.

(10) Patent No.: US 11,116,484 B2
(45) Date of Patent: Sep. 14, 2021

(54) LENS ASSEMBLY FOR 3D ELECTRONIC NASOPHARYNGOSCOPE

(71) Applicant: Hongming Zhu, Jiangsu (CN)

(72) Inventors: Hongming Zhu, Jiangsu (CN); Xia He, Jiangsu (CN)

(73) Assignee: Hongming Zhu, Jiangsu (CN)

( * ) Notice: Subject to any disclaimer, the term of this patent is extended or adjusted under 35 U.S.C. 154(b) by 407 days.

(21) Appl. No.: 16/177,377

(22) Filed: Oct. 31, 2018

(65) Prior Publication Data
US 2020/0129162 A1     Apr. 30, 2020

(51) Int. Cl.
| | | |
|---|---|---|
| A61B 1/00 | (2006.01) | |
| A61B 10/04 | (2006.01) | |
| A61B 1/233 | (2006.01) | |
| A61B 1/05 | (2006.01) | |
| A61B 1/06 | (2006.01) | |
| A61B 1/015 | (2006.01) | |
| A61B 10/00 | (2006.01) | |
| A61B 10/06 | (2006.01) | |
| A61B 1/005 | (2006.01) | |

(52) U.S. Cl.
CPC ............ *A61B 10/04* (2013.01); *A61B 1/0052* (2013.01); *A61B 1/0056* (2013.01); *A61B 1/00087* (2013.01); *A61B 1/00114* (2013.01); *A61B 1/015* (2013.01); *A61B 1/05* (2013.01); *A61B 1/0676* (2013.01); *A61B 1/233* (2013.01); *A61B 10/0051* (2013.01); *A61B 10/06* (2013.01); *A61B 1/00082* (2013.01); *A61B 1/00094* (2013.01); *A61B 1/00096* (2013.01)

(58) Field of Classification Search
None
See application file for complete search history.

(56) References Cited

U.S. PATENT DOCUMENTS

| | | | | |
|---|---|---|---|---|
| 5,351,678 A | * | 10/1994 | Clayton | A61B 1/00179 600/114 |
| 5,643,176 A | * | 7/1997 | Persidsky | A61B 1/00183 359/831 |
| 2004/0044350 A1 | * | 3/2004 | Martin | A61B 1/0057 606/139 |
| 2009/0124398 A1 | * | 5/2009 | Thompson | A61B 1/0052 464/52 |
| 2013/0310648 A1 | * | 11/2013 | Kazakevich | G02B 23/2476 600/166 |

FOREIGN PATENT DOCUMENTS

| | | |
|---|---|---|
| CN | 204445797 | 7/2015 |
| CN | 204562076 | 8/2015 |

* cited by examiner

*Primary Examiner* — Timothy J Neal
(74) *Attorney, Agent, or Firm* — JCIPRNET (57) ABSTRACT

A lens assembly includes an adjustable lens assembly including a handle. A telescopic tube is inserted at one end of the handle. A threaded rod is disposed inside the handle at an end close to the telescopic tube. An end of the threaded rod away from the telescopic tube penetrates through an outer wall of the handle and is connected to a turn button. An end of the telescopic tube inside the handle is sleeved with a driven gear. A driving gear is embedded in a surface of the handle above the driven gear. The driving gear and the driven gear enable the telescopic tube to rotate, thereby adjusting a direction of an insertion head at one end. The threaded rod and the turn button enable the telescopic rod to move within the handle, thereby adjusting the insertion head at one end to stretch out or draw back.

5 Claims, 7 Drawing Sheets

LENS ASSEMBLY FOR 3D ELECTRONIC NASOPHARYNGOSCOPE

BACKGROUND

Technical Field

The present invention relates to the technical field of medical equipment, and in particular, to a lens assembly for a 3D electronic nasopharyngoscope.

Description of Related Art

Currently, common nasopharyngoscopes include nasopharyngeal fiberscopes and electronic nasopharyngoscopes. Most nasopharyngoscopes include multiple refractive optical lenses. A combination of these optical lenses can transmit images to a photographing system, thus implementing wide-view imaging. However, such an existing optical system can only be used to observe information on the surface of nasopharynx tissues. The nasopharyngeal fiberscope and the electronic nasopharyngoscope can only achieve an observation function when being used, but cannot apply treatment means during observation. Obstruction of a nasopharynx is usually caused by the presence of a foreign matter or a lump. A patient has anoxia as the respiratory tract is obstructed, hence having dizziness, headache and other symptoms. A current clinical nasopharyngoscope examination includes following specific operations. (1) Carrying out anesthesia on the surface of the nasopharynx of the patient. (2) Slowly feeding a nasopharyngoscope from the front nostril to the nasopharynx via the bottom of the nasal cavity, and carefully observing the condition of the nasopharynx and acquiring disease information. (3) Upon detection of a foreign matter or a lump, taking out the nasopharyngoscope, feeding medical equipment capable of removing a focus of infection or extracting a biopsy specimen to the nasopharynx from the front nostril of the patient again, and removing the focus of infection or extracting the biopsy specimen to complete examination and treatment.

Currently, a structure of the conventional nasopharyngoscope commonly used clinically has following defects. (1) It can only be used to observe the nasopharynx but cannot be used for real-time treatment. (2) When using medical equipment to process the focus of infection of the nasopharynx, an operator is required to have a relatively high level of operation proficiency, and treatment effect cannot be guaranteed because there is no nasopharyngoscope for observation. (3) Since the observation and treatment are carried out separately, the medical equipment needs to be fed into the nasopharynx from the nasal cavity of the patient twice or even more times during each diagnosis and treatment, thus resulting in complex operations and greatly increasing the discomfort of the patient. (4) In examination or treatment process, secretions or blood in the nose easily blocks the camera, which affects the observation and judgment of the operator and may further affect the treatment effect in some degree. (5) Currently, all clinical nasopharyngoscopes are two-dimensional imaging systems, which cannot carry out stereo microscopic observation and analysis or real-time photographic recording for the focus of infection, and cannot implement all-around nasal, pharyngeal, and laryngeal examination over 360 degrees.

Currently, Chinese Patent Application No. 201520128045.7 discloses a novel nasopharyngoscope, which mainly solves the problem that the conventional nasopharyngoscope cannot carry out observation and treatment at the same time. The novel nasopharyngoscope includes an insertion tube, a camera, a light source, a handle, and a display portion. The camera and the light source are disposed at a front end of the insertion tube. The rear end portion of the insertion tube is connected to the handle. The rear end portion of the handle is in communication with the display portion. The display portion is connected to the camera and the light source through a circuit inside the insertion tube. A sampling tube serving as an imbibition channel or an access duct of an elongated instrument is further disposed in the insertion tube. A sampling tube outlet of the sampling tube is provided on the front end face of the insertion tube. A sampling tube inlet of the sampling tube is provided on an outer peripheral wall of the handle or the insertion tube. The present invention is simple in structure and convenient to use, and can be used for treating any detected focus of infection while examining the nasopharynx of the patient, thus reducing harm to the patient.

In addition, Chinese Patent Application No. 201520029921.0 discloses another novel nasopharyngoscope. It mainly solves the problem that the conventional nasopharyngoscope cannot dredge the nasopharynx. The novel nasopharyngoscope includes an insertion tube, a camera, a light source, a handle, and a display module. The novel nasopharyngoscope further includes an air bag arranged around a circumference of a tube wall at a front end portion of the insertion tube. After being inflated, the air bag can deform soft tissues around the nasopharynx by force, thereby expanding the space of the nasopharynx. The nasopharyngoscope further includes an air pipe at least partially disposed inside the insertion tube or in the tube wall of the insertion tube. One end of the air pipe is in communication with the air bag. The nasopharyngoscope further includes an air valve that is connected to the other end of the air pipe and used to control inflation or deflation of the air bag. The nasopharyngoscope of this invention can be used to dredge the nasopharynx during observation of the nasopharynx, thus quickly alleviating the pain of the patient. The nasopharyngoscope can also be used to treat sinuses and carry out balloon sinuplasty without using special expensive guiding tubes and balloon dilatation tubes. Moreover, the product is simple in structure and has integrated functions such as photographing, lighting, dredging, and treatment. The nasopharyngoscope is easy to operate and can be used by medical staff conveniently.

Currently, the most commonly used clinical nasopharyngoscopes are all 2D imaging systems, which cannot adjust focal lengths and magnification factors of images, and therefore cannot carry out further stereo microscopic observation and analysis for the focus of infection; moreover, real-time photographic recording cannot be performed for the nasopharynx. Hence, the development requirement of the clinical application is to realize multi-functional non-invasive imaging.

The existing nasopharyngoscope has certain defects during operation. For example, when the nasopharyngoscope is inserted into the nasopharynx, a doctor cannot observe the condition inside the nasopharynx comprehensively due to small interior space, limited observation range, and unchangeable observation direction. As a result, it is difficult to diagnose the disease, thus affecting the examination effect. In addition, during the examination, it is very inconvenient to adjust the length of an external connecting tube, and the tube needs to be fed in and pulled out manually, which causes usage inconvenience to the doctor.

The existing nasopharyngoscope transmits signals to the display screen through an electrode slice at one end during examination, thereby obtaining the position situation inside the nasopharynx. However, it is impossible to adjust the position of the electrode slice to carry out 3D surveying and mapping. Besides, one end of the nasopharyngoscope can only realize one single function, and cannot be replaced so as to carry out a sampling operation. This causes great inconvenience in use. Accordingly, a lens assembly for a 3D electronic nasopharyngoscope is proposed.

SUMMARY

An objective of the present invention is to provide a lens assembly for a 3D electronic nasopharyngoscope, so as to solve the problems proposed in the background art that the lens observation direction cannot be changed, and that it is inconvenient to adjust the length of an external connecting tube. When the nasopharyngoscope is used for examination and treatment, the condition of the nasopharynx can be observed through images transmitted in real time by an inserted photographing component, and real-time photographic recording can be carried out for the nasopharynx, which facilitates saving and playback of 3D image data after the operation is finished, so that clinicians can better analyze the disease condition. The present invention can further solve the problems proposed in the background art that the position of the electrode slice cannot be adjusted to carry out 3D surveying and mapping, and that only one single function can be implemented at one end of the nasopharyngoscope.

In order to achieve the foregoing objective, the present invention provides the following technical solutions.

A lens assembly is adapted for a 3D electronic nasopharyngoscope. The lens assembly includes an adjustable lens assembly. The adjustable lens assembly comprises a handle. The handle is of a hollow tubular structure. A telescopic tube is inserted at one end of the handle. A threaded rod is disposed inside the handle at an end close to the telescopic tube. An end of the threaded rod which is away from the telescopic tube penetrates through an outer wall of the handle and is connected to a turn button. An end of the telescopic tube which is inside the handle is sleeved with a driven gear. A driving gear is embedded in the surface of the handle which is above the driven gear. The driving gear is engaged with the driven gear, and two sides of the driving gear are connected to a housing of the handle in a rotary manner through a rotation shaft. An end of the telescopic tube which is away from the handle is bent and is connected to an air bag. A surface of the telescopic tube is connected to an air pipe. One end of the air pipe penetrates through an interior of the telescopic tube and is connected to the air bag. An end of the air bag which is away from the telescopic tube is connected to an insertion head.

A limiting gasket is sleeved over the surface at an end of the telescopic tube which is close to the threaded rod.

A camera, an imbibition tip, a light source, and a sampling inlet are sequentially arranged on a surface at one end of the insertion head.

An air blow pipe is disposed inside the insertion head. One end of the air blow pipe penetrates through an outer wall at one end of the insertion head, and an air outlet of the air blow pipe faces the camera. The other end of the air blow pipe sequentially penetrates through the insertion head and an interior of the air bag and is led out from the surface of the telescopic tube. The end of the air blow pipe which is led out from the surface of the telescopic tube is connected to an external air blower.

A support column is disposed on one side of the adjustable lens assembly. A base plate is disposed at a bottom of the support column. A connecting arm is tightly welded at a top of the support column. An L-shaped rod is tightly welded at a top of the connecting arm. A horizontal end of the L-shaped rod which is away from the connecting arm is connected to a first flexible rod through a locking button. An end of the first flexible rod which is away from the L-shaped rod is connected to a second flexible rod through a locking button. One end of the second flexible rod is tightly welded on the surface of the handle. A surface of the second flexible rod is connected to a connecting wire. An end of the connecting wire which is away from the second flexible rod is connected to a display screen.

The fixed rod is of a hollow tubular structure with an opening at one end. An inner locking rod or a sampling device is disposed at an end of the fixed rod which is close to the opening. The inner locking rod is provided with a retaining groove at a position close to the opening of the fixed rod; a connecting rod is inserted inside the retaining groove. An end of the connecting rod which is away from the inner locking rod extends out of the retaining groove and is tightly welded with a telescopic rod. An end of the telescopic rod which is away from the connecting rod is tightly welded with a tell final stud. A plurality of electrode strips are disposed between the inner locking rod and the terminal stud. A support column is disposed vertically at an end of the fixed rod which is away from the inner locking rod. A support plate is disposed at the bottom of the support column. A cross rod is tightly welded at a top of the support column. An end of the cross rod which is away from the support column is connected to an adjusting lever in a rotary manner through an adjusting screw nut. An end of the adjusting lever which is away from the cross rod is connected to a rotary rod in a rotary manner through an adjusting screw nut. An end of the rotary rod which is away from the adjusting lever is connected to the fixed rod. The inner locking rod is provided with inner limiting holes on the upper surface at both ends. The fixed rod is provided with an outer limiting hole on the outer wall close to the inner limiting hole. The connecting rod is provided with a positioning hole at a top of an end close to the inner locking rod. A limiting pin is disposed at the top of an end of the inner locking rod which is close to the connecting rod. The limiting pin sequentially penetrates through the outer limiting hole, the inner limiting hole, and the positioning hole.

The rotary rod is externally connected to a connecting wire, and one end of the connecting wire is connected to a display screen.

An elastic cushion is disposed on an inner wall of the retaining groove. The electrode strips are disposed in a bent manner. One end of the electrode strip is tightly welded with one end of the inner locking rod, and the other end of the electrode strip is tightly welded with the terminal stud. A plurality of electrode slices arranged at equal intervals are embedded in a surface of the electrode strip.

The sampling device comprises a fixed column. One end of the fixed column is connected to an outer tube. An end of the outer tube which is away from the fixed column is connected to a jaw holder. Jaws are disposed at an end of the jaw holder which is away from the outer tube. The outer tube is of a spiral structure.

Compared with the prior art, the present invention has following beneficial effects.

In the present invention, the electrode strips disposed in the lens assembly allow the electrode slices to be arranged in three dimensions at one end of the device, thereby facilitating the surveying and mapping operation. The sampling device disposed in the lens assembly allows the lens assembly to implement various functions, so that one end of the lens assembly can be replaced at any time to carry out a sampling operation.

A lens assembly for a 3D electronic nasopharyngoscope according to the present invention includes a fixed rod. An inner locking rod is disposed at an end of the fixed rod which is close to the opening. The inner locking rod is provided with a retaining groove at a position close to the opening of the fixed rod. A connecting rod is inserted in the retaining groove. An end of the connecting rod which is away from the inner locking rod extends out of the retaining groove and is tightly welded with a telescopic rod. An end of the telescopic rod which is away from the connecting rod is tightly welded with a terminal stud. A plurality of electrode strips is disposed between the inner locking rod and the terminal stud. The inner locking rod is provided with inner limiting holes on the upper surface at both ends. The fixed rod is provided with an outer limiting hole on the outer wall close to the inner limiting hole. The connecting rod is provided with a positioning hole at the top of an end close to the inner locking rod. The present invention is simple in structure and convenient to use. The electrode strips allow the electrode slices to be arranged in three dimensions at one end of the device, thereby facilitating the surveying and mapping operation. The sampling device allows the lens assembly to implement various functions, so that one end of the lens assembly can be replaced at any time to carry out a sampling operation.

In the present invention, the driving gear and the driven gear disposed in the lens assembly can enable the telescopic tube to rotate, thereby adjusting the direction of the insertion head at one end, so that the doctor can observe the condition inside the nasopharynx more conveniently. The threaded rod and the turn button disposed in the lens assembly can enable the telescopic rod to rotate inside the handle, thereby adjusting the insertion head at one end to stretch out or draw back, so that the insertion head is controlled more conveniently and precisely. The present invention has great practical value and is easy to promote.

The present invention proposes a 3D electronic nasopharyngoscope. When the nasopharyngoscope is used for examination and treatment, the condition of the nasopharynx can be observed through images transmitted in real time by an inserted photographing component, and real-time photographic recording can be carried out for the nasopharynx, which facilitates saving and playback of 3D image data after the operation is finished, so that clinicians can better analyze the disease condition.

The present invention is provided with an imbibition tube, an imbibition tip, and a drain outlet, and therefore matters that obstruct the camera can be effectively eliminated, so that a photographing effect of the camera is clearer.

The present invention is provided with a sampling piece and a sampling tube in coordination with the sampling piece, so that sampling can be performed at any time, the operation is convenient, and the precision of the pathological analysis can be improved.

The structure of the present invention is easy to adjust. Moreover, nursing staff are effectively prevented from touching the present invention while doctors will not be affected. The present invention is highly safe in use.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Technical solutions in the embodiments of the present invention will be described clearly and completely with reference to the accompanying drawings in the embodiments of the present invention. Obviously, the described embodiments are only some rather than all of the embodiments of the present invention. All other embodiments derived by a person of ordinary skill in the art based on the embodiments in the present invention without making creative efforts should belong to the protection scope of the present invention.

In the description of the present invention, it should be understood that orientations or positional relations indicated by terms such as "center", "longitudinal", "traversal", "length", "width", "thickness", "upper", "lower", "front", "rear", "left", "right", "vertical", "horizontal", "top", "bottom", "inner", "outer", "clockwise", and "anticlockwise" are orientations or positional relations based on the drawings, and are merely used for describing the present invention conveniently and simplifying the description but do not indicate or imply that the indicated devices or elements should have particular orientations or should be constructed and operated at particular orientations. Therefore, such terms should not be construed as limitations on the present invention.

In addition, terms such as "first" and "second" are merely used for the purpose of description, and cannot be construed as indicating or implying relative importance or implicitly indicating the quantity of the indicated technical features. Therefore, a feature limited by "first" or "second" can include one or more said features implicitly or explicitly. In the description of the present invention, the term "multiple" means two or more than two, unless otherwise specified.

Referring to FIG. 1 to FIG. 4, the present invention provides a technical solution as follows.

Embodiment 1

Figure 2:
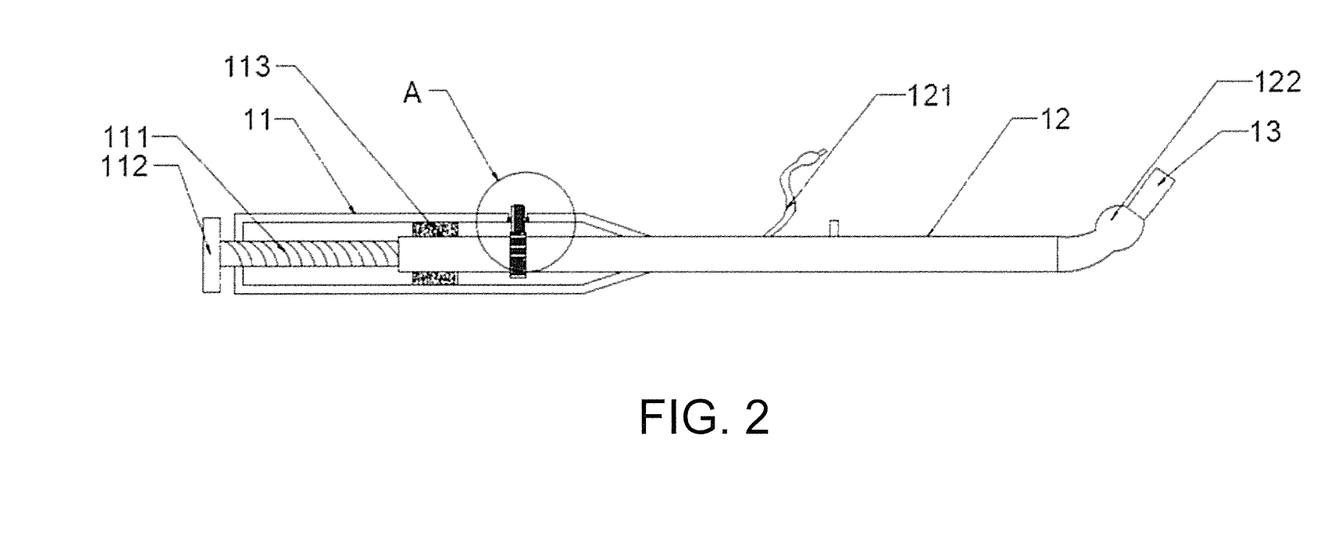
FIG. 2 is a schematic structural diagram of an adjustable lens assembly in the present invention.
Figure 3:
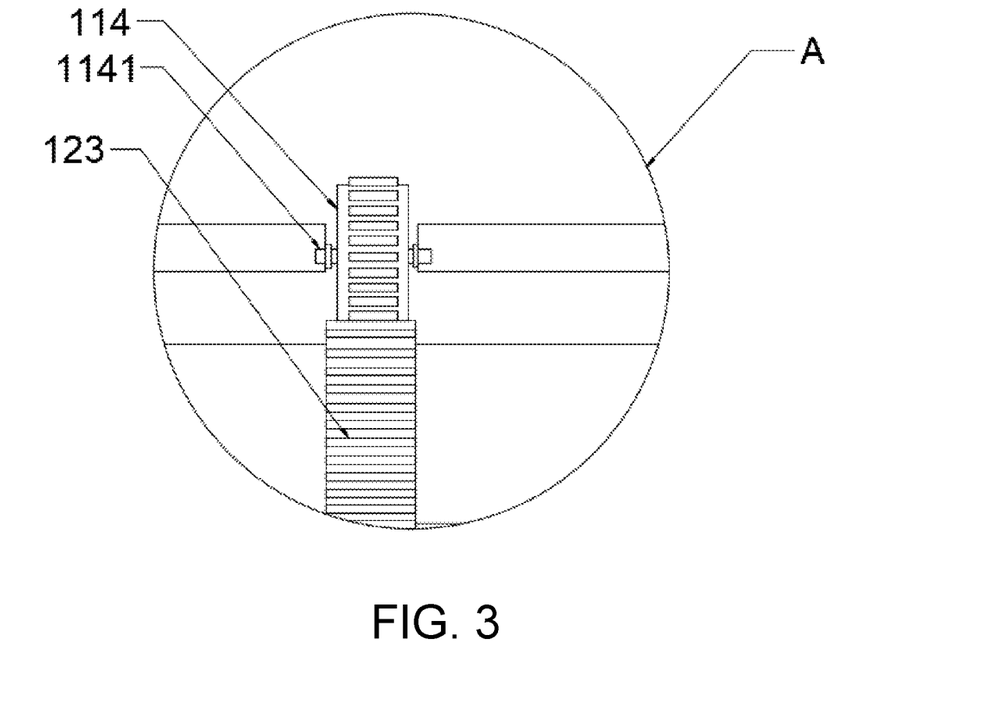
FIG. 3 is a partial enlarged diagram of point A in FIG. 2 according to the present invention.

As shown in FIG. 2 and FIG. 3, a lens assembly for a 3D electronic nasopharyngoscope includes an adjustable lens assembly 1. The adjustable lens assembly 1 includes a handle 11. The handle 11 is of a hollow tubular structure. A telescopic tube 12 is inserted at one end of the handle 11. A threaded rod 111 is disposed inside the handle 11 at an end close to the telescopic tube 12. An end of the threaded rod 111 which is away from the telescopic tube 12 penetrates through an outer wall of the handle 11 and is connected to a turn button 112. An end of the telescopic tube 12 which is inside the handle 11 is sleeved with a driven gear 123. A driving gear 114 is embedded in the surface of the handle 11 which is above the driven gear 123. The driving gear 114 is engaged with the driven gear 123, and two sides of the driving gear 114 are connected to a housing of the handle 11 in a rotary manner through a rotation shaft 1141.

Further, a surface of the threaded rod 111 is in threaded connection with the side wall of the handle 11. Through the rotation of the threaded rod, the telescopic tube 12 can be controlled to move left and right.

It should be noted that, as shown in FIG. 2, an end of the telescopic tube 12 which is away from the handle 11 is bent and is connected to an air bag 122. A surface of the telescopic tube 12 is connected to an air pipe 121. One end of the air pipe 121 penetrates through an interior of the telescopic tube 12 and is connected to the air bag 122. An end of the air bag 122 which is away from the telescopic tube 12 is connected to an insertion head 13. A limiting gasket 113 is sleeved over the surface at an end of the telescopic tube 12 which is close to the threaded rod 111.

In this embodiment, the air bag 122 is made of a rubber material. The rubber has characteristics such as good elasticity, insulation, watertightness, and airtightness, and can expand when being filled with air, so that an inner space of a nasopharynx is enlarged, thereby facilitating observation.

In addition, the limiting gasket 113 is made of a polyurethane foaming material, and has a soft structure and a good cushioning function. The limiting gasket 113 can help the telescopic rod 12 stay stationary in a vertical direction when the telescopic rod 12 is moving left and right, thereby ensuring stability of the telescopic rod 12 when it enters into the nasopharynx.

Figure 4:
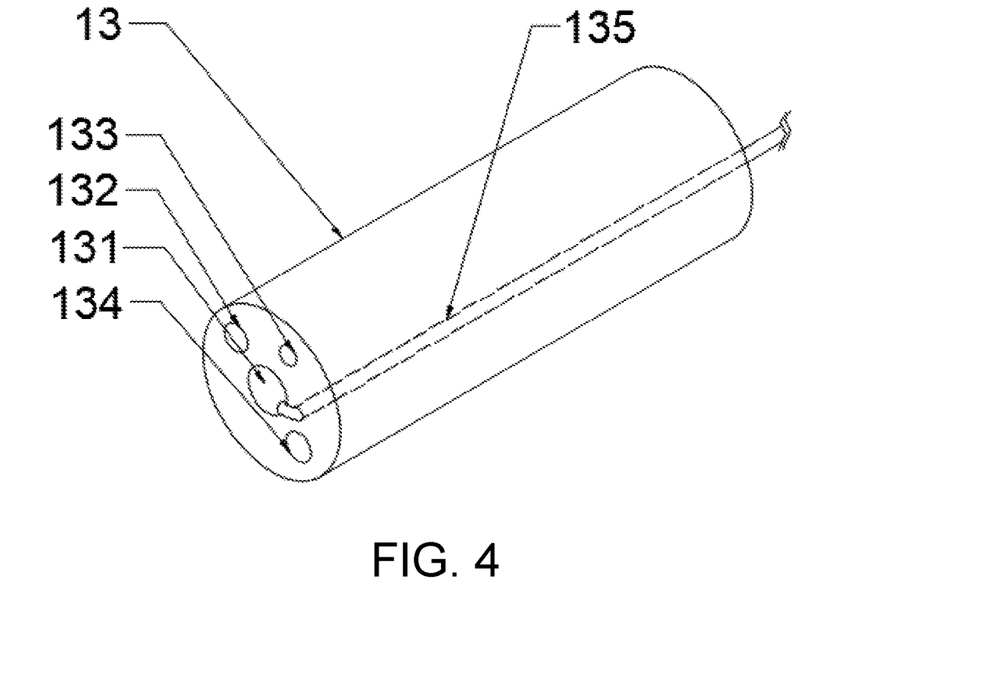
FIG. 4 is a 3D schematic structural diagram of an insertion head in the present invention.

It should be noted that, as shown in FIG. 2 and FIG. 4, a camera 131, an imbibition tip 132, a light source 133, and a sampling inlet 134 are sequentially arranged on a surface at one end of the insertion head 13. An air blow pipe 135 is disposed inside the insertion head 13. One end of the air blow pipe 135 penetrates through the outer wall at one end of the insertion head 13, and an air outlet of the air blow pipe 135 faces the camera 131. The other end of the air blow pipe 135 sequentially penetrates through the insertion head 13 and an interior of the air bag 122 and is led out from the surface of the telescopic tube 12. The end of the air blow pipe 135 which is led out from the surface of the telescopic tube 12 is connected to an external air blower.

Specifically, the air blow pipe 135 is made of a PVC material, which has been used as a medical material for many years. The PVC material is resistant to chemical corrosion, and has strong resistance against oxidants, reductants, and strong acid. Moreover, the PVC material is wear-resisting, easy to produce, safe to use, and cheap in cost, and can greatly prolong the service life of the air blow pipe 135. The air blow pipe 135 can automatically demist the camera 131 after the air blower is connected to one end of the air blow pipe 135.

Figure 1:
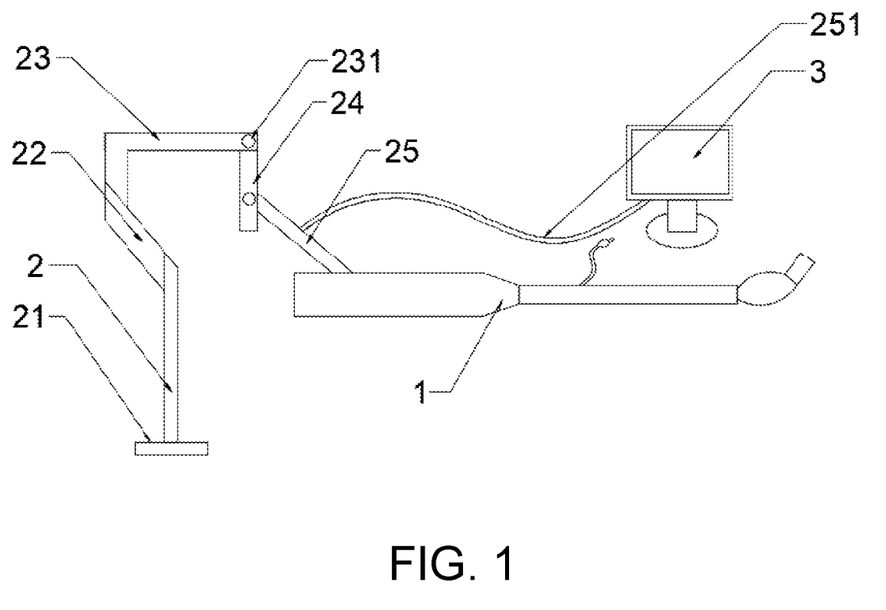
FIG. 1 is an overall schematic structural diagram of the present invention.

As shown in FIG. 1, a support column 2 is disposed on one side of the adjustable lens assembly 1. A base plate 21 is disposed at a bottom of the support column 2. A connecting arm 22 is tightly welded at a top of the support column 2. An L-shaped rod 23 is tightly welded at the top of the connecting arm 22. A horizontal end of the L-shaped rod 23 which is away from the connecting arm 22 is connected to a first flexible rod 24 through a locking button 231. An end of the first flexible rod 24 which is away from the L-shaped rod 23 is connected to a second flexible rod 25 through a locking button 231. One end of the second flexible rod 25 is tightly welded on the surface of the handle 11. A connecting wire 251 is connected on the surface of the second flexible rod 25. An end of the connecting wire 251 which is away from the second flexible rod 25 is connected to a display screen 3, and the other end of the connecting wire 251 passes through the interior of the telescopic rod 12 and is connected to the camera 131.

The working principle of the present invention is as follows. When the device is used, the support column 2 is vertically placed on a ground and is supported by the base plate 21. An angle of the handle 11 is adjusted in a wide range through the first flexible rod 24 and the second flexible rod 25. The insertion head at one end of the telescopic rod 12 is slowly inserted into the nasopharynx. Turning of the turn button 112 can enable the threaded rod 111 to move, so that the telescopic rod 12 enters into the nasopharynx slowly. Therefore, the doctor can control the process conveniently. After the telescopic rod 12 enters into the nasopharynx, the doctor observes the condition inside the nasopharynx through the camera 131. When an internal angle needs to be adjusted, the doctor rotates the driving gear 114. The driving gear 114 drives the driven gear 123 to rotate, so that the telescopic tube 12 is rotated. The direction of the camera 131 is thus deflected, so that the doctor can observe the condition around 360°. Signals received by the camera 131 are transmitted to the display screen 3 through the connecting wire 251. An internal 3D image is specifically analyzed and observed through the display screen 3. After observation, imbibition and sampling operations are performed by using the imbibition tip 132 and the sampling inlet 134. When mist is generated on a surface of the camera 131 and it is inconvenient to observe the nasopharynx, the air blower is connected to one end of the air blow pipe 135. Air is blown into the nasopharynx through the air blow pipe 135 and sprayed over the surface of the camera 131 to automatically remove the mist. The camera 131 of the device can transmit 3D images inside the nasopharynx to the display screen, so that the disease condition is observed more precisely.

Second Embodiment

Figure 5:
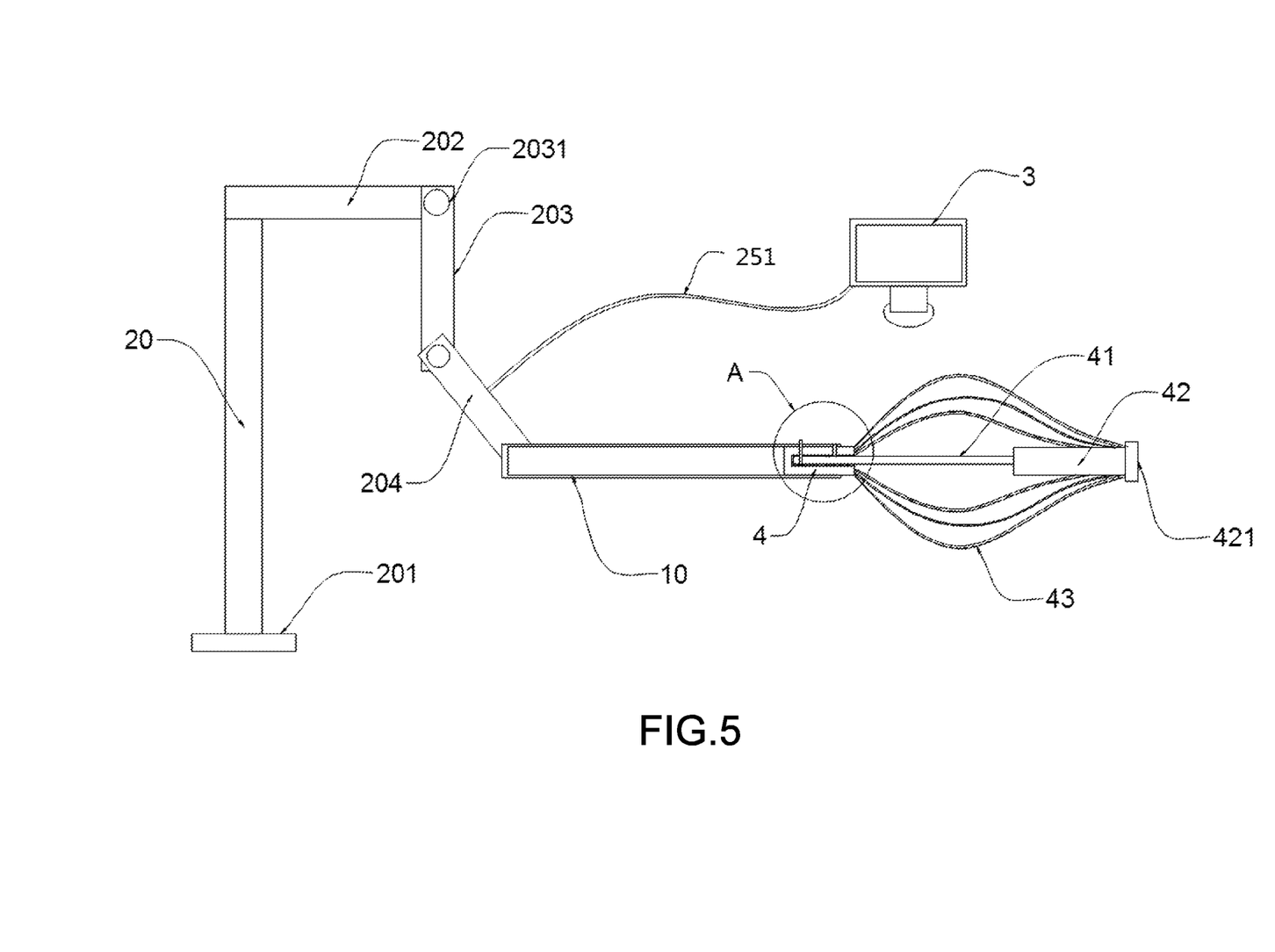
FIG. 5 is an overall schematic structural diagram of a second embodiment of the present invention.
Figure 6:
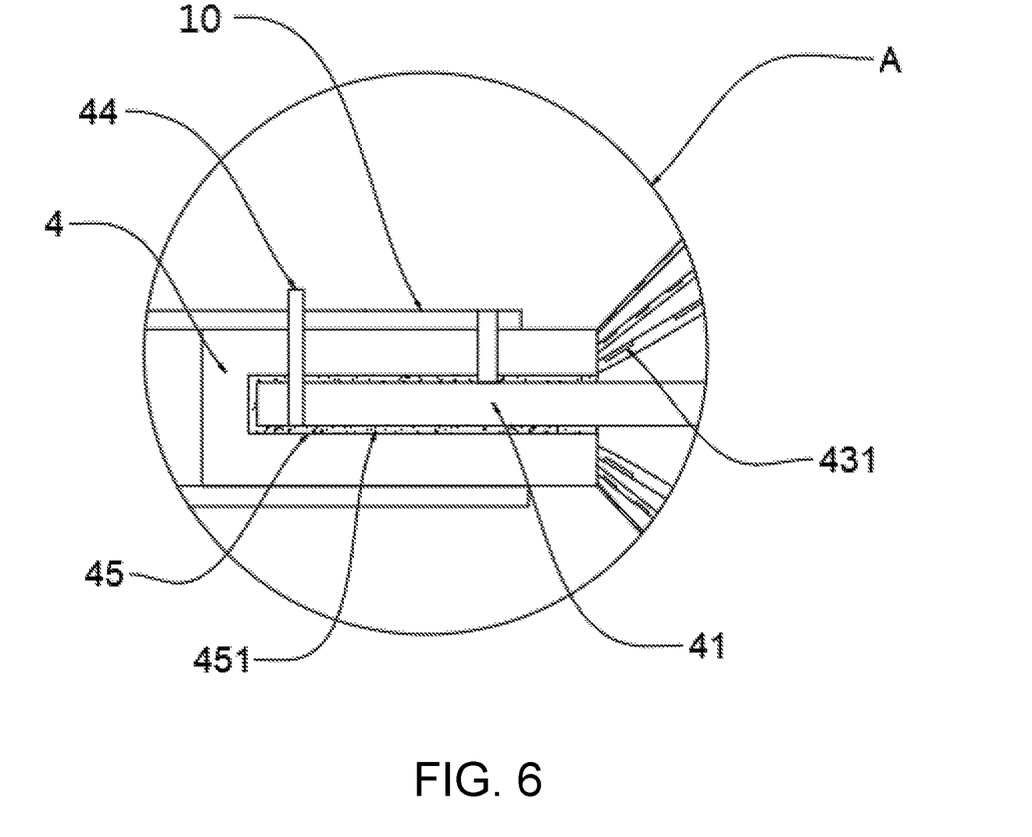
FIG. 6 is a partial enlarged diagram of point A in FIG. 5 according to the present invention.
Figure 7:
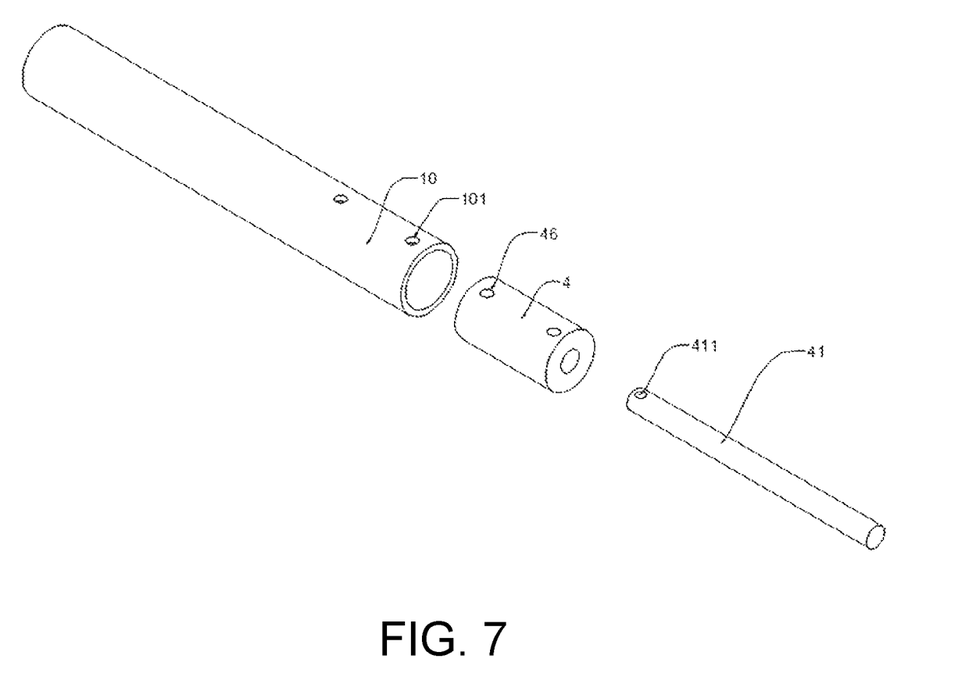
FIG. 7 is an exploded structural diagram of a fixed rod, an inner locking rod, and a connecting rod in the present invention.

As shown in FIG. 5 to FIG. 7, a lens assembly for a 3D electronic nasopharyngoscope includes a fixed rod 10. The fixed rod 10 is of a hollow tubular structure with an opening at one end. An inner locking rod 4 or a sampling device 5 is disposed at an end of the fixed rod 10 which is close to the opening. The inner locking rod 4 is provided with a retaining groove 45 at a position close to the opening of the fixed rod 10. An elastic cushion 451 is disposed on an inner wall of the retaining groove 45. A connecting rod 41 is inserted inside the retaining groove 45. An end of the connecting rod 41 which is away from the inner locking rod 4 extends out of the retaining groove 45 and is tightly welded with a telescopic rod 42. An end of the telescopic rod 42 which is away from the connecting rod 41 is tightly welded with a terminal stud 421. A plurality of electrode strips 43 are disposed between the inner locking rod 4 and the terminal stud 421. The electrode strip 43 is disposed in a bent manner and made of a rubber material. One end of the electrode strip 43 is tightly welded with an end of the inner locking rod 4, and the other end of the electrode strip 43 is tightly welded with the terminal stud 421. A plurality of electrode slices 431 arranged at equal intervals are embedded in a surface of the electrode strip 43. The electrode slices 431 are used for mapping, collecting 3D coordinates in the nasal cavity, and forming 3D images after graphic software processing.

In this embodiment, each electrode slice 431 has an independent conductive wire. The conductive wires pass through the interior of the insulating electrode strip 43 and are finally gathered in the fixed rod 10 at one end; then, the conductive wires are further connected to an external socket.

As shown in FIG. 5, a support column 20 is disposed vertically at the end of the fixed rod 10 which is away from the inner locking rod 4. A support plate 201 is disposed at a bottom of the support column 20. A cross rod 202 is tightly welded at the top of the support column 20. An end of the cross rod 202 which is away from the support column 20 is connected to an adjusting lever 203 in a rotary manner through an adjusting screw nut 2031. An end of the adjusting lever 203 which is away from the cross rod 202 is connected to a rotary rod 204 in a rotary manner through an adjusting screw nut 2031. An end of the rotary rod 204 which is away from the adjusting lever 203 is connected to the fixed rod 10. The rotary rod 204 is connected to an external connecting wire 251, and one end of the connecting wire 251 is connected to a display screen 3.

Specifically, a P5 high-definition display screen produced by Anhui Hongfeng Electronic Technology Co., Ltd. can be employed as the display screen 3. Support circuits of the display screen 3 can also be provided by the vendor.

In addition, a RPS linear sensor produced by Apollo Electronics (Shenzhen) Co., Ltd. can be employed as the electrode slice 431, and support circuits thereof can also be provided by the vendor. The electrode slice 431 can output sensed position signals. An external side of the electrode slice 431 is connected to an STM32F0 single-chip microprocessor. The single-chip microprocessor is connected to the display screen 3 through a wire. The signal from the electrode slice 431 is processed by the single-chip microprocessor, so that the signal is transmitted to the display screen 3 for display, thereby implementing 3D surveying and mapping.

As shown in FIG. 6 and FIG. 7, the inner locking rod 4 is provided with inner limiting holes 46 on the upper surface at both ends. The fixed rod 10 is provided with an outer limiting hole 101 on the outer wall close to the inner limiting hole 46. The connecting rod 41 is provided with a positioning hole 411 at the top of an end close to the inner locking rod 4. A limiting pin 44 is disposed at the top of an end of the inner locking rod 4 which is close to the connecting rod 41. The limiting pin 44 sequentially penetrates through the outer limiting hole 101, the inner limiting hole 46 and the positioning hole 411.

In this embodiment, the telescopic rod 42 is stretched out and drawn back, so that the electrode strip 43 is straightened and bent. The straightening and bending of the electrode strip 43 can change the position of the electrode slice 431 on the surface of the electrode strip 43, thereby implementing 3D surveying and mapping. When the electrode strip 43 is straightened or bent to a predetermined position, the limiting pin 44 sequentially penetrates through the outer limiting hole 101, the inner limiting hole 46 and the positioning hole 411, so that the inner locking rod 4 is fixed.

Third Embodiment

Figure 8:
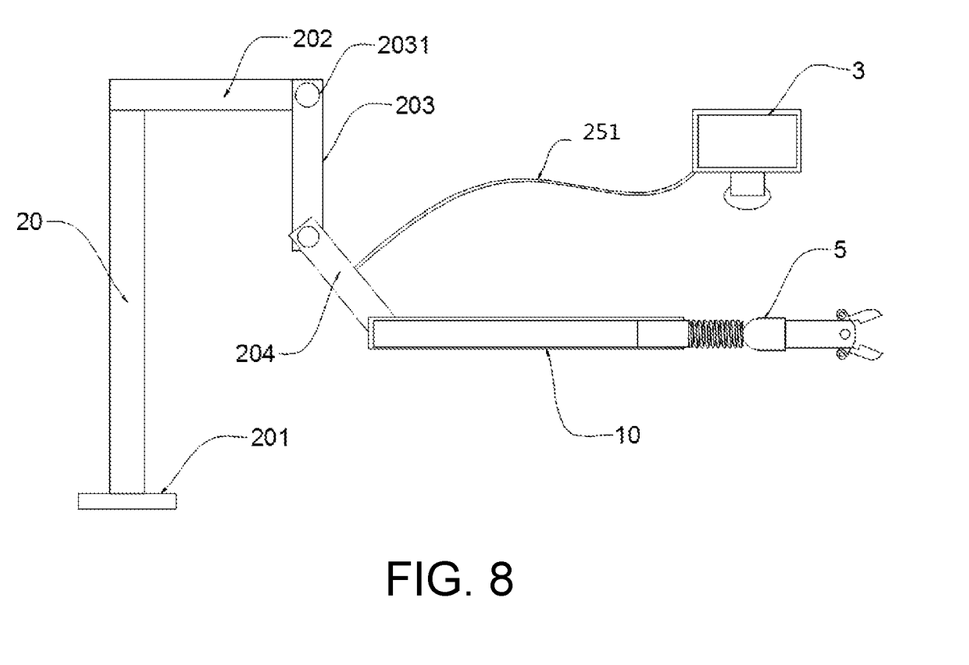
FIG. 8 is an overall schematic structural diagram of a third embodiment of the present invention.
Figure 9:
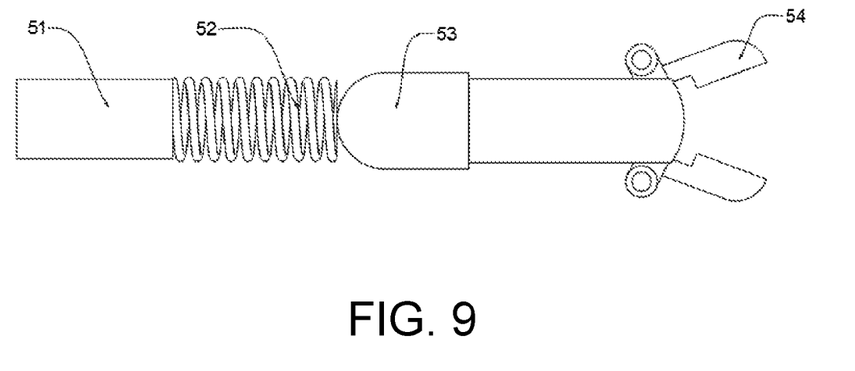
FIG. 9 is a schematic structural diagram of a sampling device in the present invention.

In a specific using process, the end of the fixed rod 10 is incapable of carrying out a sampling operation, and an additional sampling device needs to be used. Therefore, changes are made based on the second embodiment. As shown in FIG. 8 and FIG. 9, a sampling device 5 is disposed at a front end of the fixed rod 10. The sampling device 5 includes a fixed column 51. One end of the fixed column 51 is connected to an outer tube 52. An end of the outer tube 52 which is away from the fixed column 51 is connected to a jaw holder 53. Jaws 54 are disposed at an end of the jaw holder 53 which is away from the outer tube 52. The outer tube 52 is of a spiral structure.

In this embodiment, the outer tube 52 is made of a rubber material, which has certain elasticity and can achieve a good cushioning function.

Specifically, the jaws 54 can perform clamping operations to facilitate picking. Moreover, the fixed column 51 and the fixed rod 10 cooperate with each other by means of insertion, which facilitates disassembling and replacement operations.

The working principle of the present invention is as follows. When the device is used, the support column 20 is vertically placed on the plane and is supported by the support plate 201. The adjusting lever 203 and the rotary rod 204 can be rotated by using the adjusting screw nut 2031, so as to adjust the position of the fixed rod 10. After the adjustment, one end of the fixed rod 10 enters into the nasopharynx of a patient for observation. The telescopic rod 42 is stretched out or drawn back to straighten or bend the electrode strip 43. The straightening and bending of the electrode strip 43 can change the position of the electrode slice 431 on the surface of the electrode strip 43. The electrode strip 431 can transmit a sensed position signal. One side of the electrode strip is connected to the STM32F0 single-chip microprocessor. After being processed by the single-chip microprocessor, the signal is transmitted to the display screen 3 for display, thereby implementing 3D surveying and mapping. When the electrode strip 43 is straightened or bent to a predetermined position, the limiting pin 44 sequentially penetrates through the outer limiting hole 101, the inner limiting hole 46, and the positioning hole 411, so that the inner locking rod 4 is fixed. When sampling needs to be performed, the limiting pin 44 is removed, so that the inner locking rod 4 is moved out. The fixed column 51 at one end of the sampling device 5 is inserted into the fixed rod 10. The clamping operation can be carried out by using the jaws 54, thus facilitating picking. Moreover, the fixed column 51 and the fixed rod 10 cooperate with each other by means of insertion, which facilitates disassembling, and replacement operations.

Basic principles and main features of the present invention as well as advantages of the present invention are displayed and described above. A person skilled in the field should understand that the present invention is not limited by the foregoing embodiments. The foregoing embodiments and the embodiments described in the specification are merely exemplary embodiments of the present invention, which are not intended to limit the present invention. The present invention further has various changes and improvements without departing from the principle and scope of the present invention, and all these changes and improvements should fall within the scope of the present invention to be protected. The protection scope of the present invention is defined by the appended claims and equivalents of the claims.

What is claimed is:

1. A lens assembly for a 3D electronic nasopharyngoscope, the lens assembly comprising an adjustable lens assembly, wherein the adjustable lens assembly comprises a handle, a telescopic tube and an insertion head, the handle is of a hollow tubular structure; the telescopic tube is inserted at one end of the handle; a threaded rod is disposed inside the handle and connected to the telescopic tube; an end of the threaded rod which is away from the telescopic tube penetrates through an outer wall of the handle and is connected to a turn button; an end of the telescopic tube which is inside the handle is coupled with a driven gear, and the driven gear is disposed around the end of the telescopic tube;

a driving gear is embedded in a surface of the handle which is above the driven gear; the driving gear is engaged with the driven gear, and two sides of the driving gear are connected to a housing of the handle in a rotary manner through a rotation shaft; and an end of the telescopic tube which is away from the handle is bent and is connected to an inflatable component; a surface of the telescopic tube is connected to an air pipe; one end of the air pipe penetrates through an interior of the telescopic tube and is connected to the inflatable component, and an end of the inflatable component which is away from the telescopic tube is connected to the insertion head.

2. The lens assembly for a 3D electronic nasopharyngoscope according to claim 1, wherein an O-ring is sleeved over the surface at an end of the telescopic tube which is close to the threaded rod.

3. The lens assembly for a 3D electronic nasopharyngoscope according to claim 1, wherein a camera, an imbibition tip, a light source, and a sampling inlet are sequentially arranged on a surface at one end of the insertion head.

4. The lens assembly for a 3D electronic nasopharyngoscope according to claim 3, wherein:

an air blow pipe is disposed inside the insertion head; one end of the air blow pipe penetrates through an outer wall at one end of the insertion head, and an air outlet of the air blow pipe faces the camera;

the other end of the air blow pipe sequentially penetrates through the insertion head and an interior of the inflatable component and is led out from the surface of the telescopic tube, and the end of the air blow pipe which is led out from the surface of the telescopic tube is connected to an external air blower.

5. The lens assembly for a 3D electronic nasopharyngoscope according to claim 1, wherein:

a support column is disposed on one side of the adjustable lens assembly; a base plate is disposed at a bottom of the support column; a connecting arm is welded at a top of the support column; an L-shaped rod is welded at a top of the connecting arm; a horizontal end of the L-shaped rod which is away from the connecting arm is connected to a first flexible rod through a locking button;

an end of the first flexible rod which is away from the L-shaped rod is connected to a second flexible rod through a locking button; one end of the second flexible rod is welded on the surface of the handle;

a surface of the second flexible rod is connected to a connecting wire, and an end of the connecting wire which is away from the second flexible rod is connected to a display screen.

* * * * *